(12) United States Patent
Hayatsu et al.

(10) Patent No.: US 8,866,098 B2
(45) Date of Patent: Oct. 21, 2014

(54) RADIATION DETECTING UNIT

(75) Inventors: Kenzo Hayatsu, Hamamatsu (JP);
 Mitsutoshi Sugiya, Hamamatsu (JP);
 Keisuke Nagura, Hamamatsu (JP);
 Shigeru Suzuki, Hamamatsu (JP)

(73) Assignee: Hamamatsu Photonics K.K.,
 Hamamatsu-shi, Shizuoka (JP)

( * ) Notice: Subject to any disclaimer, the term of this patent is extended or adjusted under 35 U.S.C. 154(b) by 438 days.

(21) Appl. No.: 13/322,314

(22) PCT Filed: Mar. 26, 2010

(86) PCT No.: PCT/JP2010/055390
§ 371 (c)(1),
(2), (4) Date: Dec. 16, 2011

(87) PCT Pub. No.: WO2010/137396
PCT Pub. Date: Dec. 2, 2010

(65) Prior Publication Data
US 2012/0097857 A1    Apr. 26, 2012

(30) Foreign Application Priority Data

May 28, 2009  (JP) ................................ P2009-129084

(51) Int. Cl.
  *G01T 1/20*   (2006.01)
  *H01L 31/0232* (2014.01)
  *H01L 27/146* (2006.01)
  *A61B 6/03*   (2006.01)
  *A61B 6/00*   (2006.01)

(52) U.S. Cl.
  CPC ............ *H01L 31/02322* (2013.01); *G01T 1/20* (2013.01); *A61B 6/032* (2013.01); *A61B 6/4208* (2013.01); *G01T 1/2018* (2013.01); *H01L 27/14618* (2013.01); *H01L 27/14636* (2013.01); *H01L 27/14661* (2013.01); *H01L 27/14663* (2013.01)

USPC ................................ 250/370.11; 250/370.09

(58) Field of Classification Search
CPC ................................ G01T 1/20; G01T 1/2006
USPC ........................................ 250/370.09, 370.11
See application file for complete search history.

(56) References Cited

U.S. PATENT DOCUMENTS

2002/0011572 A1  1/2002  Kajiwara et al.
2005/0139757 A1  6/2005  Iwanczyk et al.

FOREIGN PATENT DOCUMENTS

DE        102 35 332      2/2004
DE     10 2005 014 087    10/2006
(Continued)

*Primary Examiner* — Casey Bryant
(74) *Attorney, Agent, or Firm* — Drinker Biddle & Reath LLP

(57) ABSTRACT

An object is to prevent occurrence of an insensitive zone to radiation in parallel arrangement of multiple units. This radiation detecting unit 1 is provided with a PD array 5 including a plurality of PD elements 13 arrayed opposite to a scintillator 3 and output electrode pads 23 arrayed corresponding to the PD elements 13, integrated circuits 7 for processing signals from the PD elements 13, a flexible substrate 9 for mounting of the PD array 5 and integrated circuits 7, and a radiation shield plate 11 provided opposite to the PD array 5 with the flexible substrate 9 in between and formed so that ends thereof 11*a* are located inside the PD array 5; the output electrode pads 23 have an array pitch made shorter than that of PD elements 13; the flexible substrate 9 is folded along the ends 11*a* at intermediate regions $A_3$ between mounting regions of the PD array 5 and integrated circuits 7, whereby the integrated circuits 7 are arranged on the opposite side to the PD elements 13 with the radiation shield plate 11 in between.

6 Claims, 8 Drawing Sheets

(56) References Cited

FOREIGN PATENT DOCUMENTS

| | | |
|---|---|---|
| JP | 9-288184 | 11/1997 |
| JP | 2002-267758 | 9/2002 |
| JP | 2003-046862 | 2/2003 |
| JP | 2003-264280 | 9/2003 |
| JP | 2004-055574 | 2/2004 |
| JP | 2004-265883 | 9/2004 |
| JP | 2004-536313 | 12/2004 |
| JP | 2006-215028 | 8/2006 |
| WO | WO 2007/117799 | 10/2007 |

RADIATION DETECTING UNIT

TECHNICAL FIELD

The present invention relates to a radiation detecting unit for detecting radiation.

BACKGROUND ART

Devices for detecting radiation such as X-rays have been used heretofore in usage such as medical use. For example, in the photoelectric conversion device described in Patent Literature 1 below, fluorescence emitted by a scintillator according to irradiation with X-rays is photoelectrically converted by photoelectric conversion elements and signal charges are transferred to a processing IC. Some of incident X-rays are not converted into fluorescence in the scintillator and pass through it, and this photoelectric conversion device is configured with a radiation absorber interposed between an insulating substrate on which the photoelectric conversion elements are arranged and a circuit board on which the IC is arranged, thereby to prevent the X-rays passing through the insulating substrate from impinging upon the IC. Signals from the photoelectric conversion elements are sent through a flexible cable to the IC.

CITATION LIST

Patent Literature

Patent Literature 1: Japanese Patent Application Laid-open No. 9-288184

SUMMARY OF INVENTION

Technical Problem

When units for detection of radiation are used as incorporated in an X-ray CT device or the like, the units are two-dimensionally arrayed in parallel (or tiled) in order to increase the number of slices. However, in the case where the conventional photoelectric conversion devices as described above are tiled in the CT device, it is necessary to secure a space for connection between the photoelectric conversion elements and the IC with the radiation absorber in between, between the photoelectric conversion elements of adjacent units. For this reason, there is a tendency to produce an insensitive region to radiation between the photoelectric conversion elements of adjacent units.

Therefore, the present invention has been accomplished in view of the above-described problem and it is an object of the present invention to provide a radiation detecting unit allowing prevention of occurrence of an insensitive zone to radiation in parallel arrangement of multiple units.

Solution to Problem

In order to solve the above problem, a radiation detecting unit according to the present invention is a radiation detecting unit comprising: a photoelectric conversion section arranged in proximity to a scintillator and including a plurality of photoelectric conversion elements arrayed along a first surface opposed to the scintillator, and a plurality of electrodes for output of signals arrayed on a second surface opposite to the first surface corresponding to the plurality of photoelectric conversion elements; a signal processing circuit for processing signals from the plurality of photoelectric conversion elements; a flexible substrate on which the photoelectric conversion section and the signal processing circuit are mounted and which electrically connects the plurality of electrodes of the photoelectric conversion section to the signal processing circuit; and a radiation shield plate provided opposite to the second surface of the photoelectric conversion section with the flexible substrate in between and formed so that an end thereof in a direction along the second surface is located inside the photoelectric conversion section, wherein the plurality of electrodes have an array pitch on the second surface made shorter than an array pitch of the photoelectric conversion elements by a wiring member, and wherein the flexible substrate is folded along the end of the radiation shield plate, at an intermediate region between a mounting region of the photoelectric conversion section and a mounting region of the signal processing circuit, whereby the signal processing circuit is arranged on the opposite side to the photoelectric conversion elements with the radiation shield plate in between.

In the radiation detecting unit as described above, light of predetermined wavelength emitted from the scintillator according to incidence of radiation is incident into the first surface of the photoelectric conversion section, the light is converted into electric signals by the plurality of photoelectric conversion elements on the first surface, and the electric signals are sent from the electrodes provided on the second surface corresponding to the photoelectric conversion elements, via the flexible circuit board to the signal processing circuit. On that occasion, the radiation passing through the photoelectric conversion elements is blocked by the radiation shield plate provided opposite to the photoelectric conversion section with the flexible substrate in between, so as to prevent adverse effect on the signal processing circuit. Furthermore, since the end of the radiation shield plate is located inside the second surface of the photoelectric conversion section and the array pitch of the electrodes on the second surface of the photoelectric conversion section is made shorter than the array pitch of the photoelectric conversion elements on the first surface, the connection range (mounting region) to the photoelectric conversion section on the flexible substrate is narrower than the second surface and the flexible substrate is folded along the end of the radiation shield plate, which eliminates the need for a space for routing of connection between the photoelectric conversion section and the signal processing circuit outside the second surface of the photoelectric conversion section. This allows prevention of occurrence of an insensitive zone between the photoelectric conversion elements of adjacent units even in the case where the radiation detecting units are tiled.

Advantageous Effect of Invention

The present invention achieves prevention of occurrence of the insensitive zone to radiation in parallel arrangement of multiple units.

DESCRIPTION OF EMBODIMENTS

Figure 1:
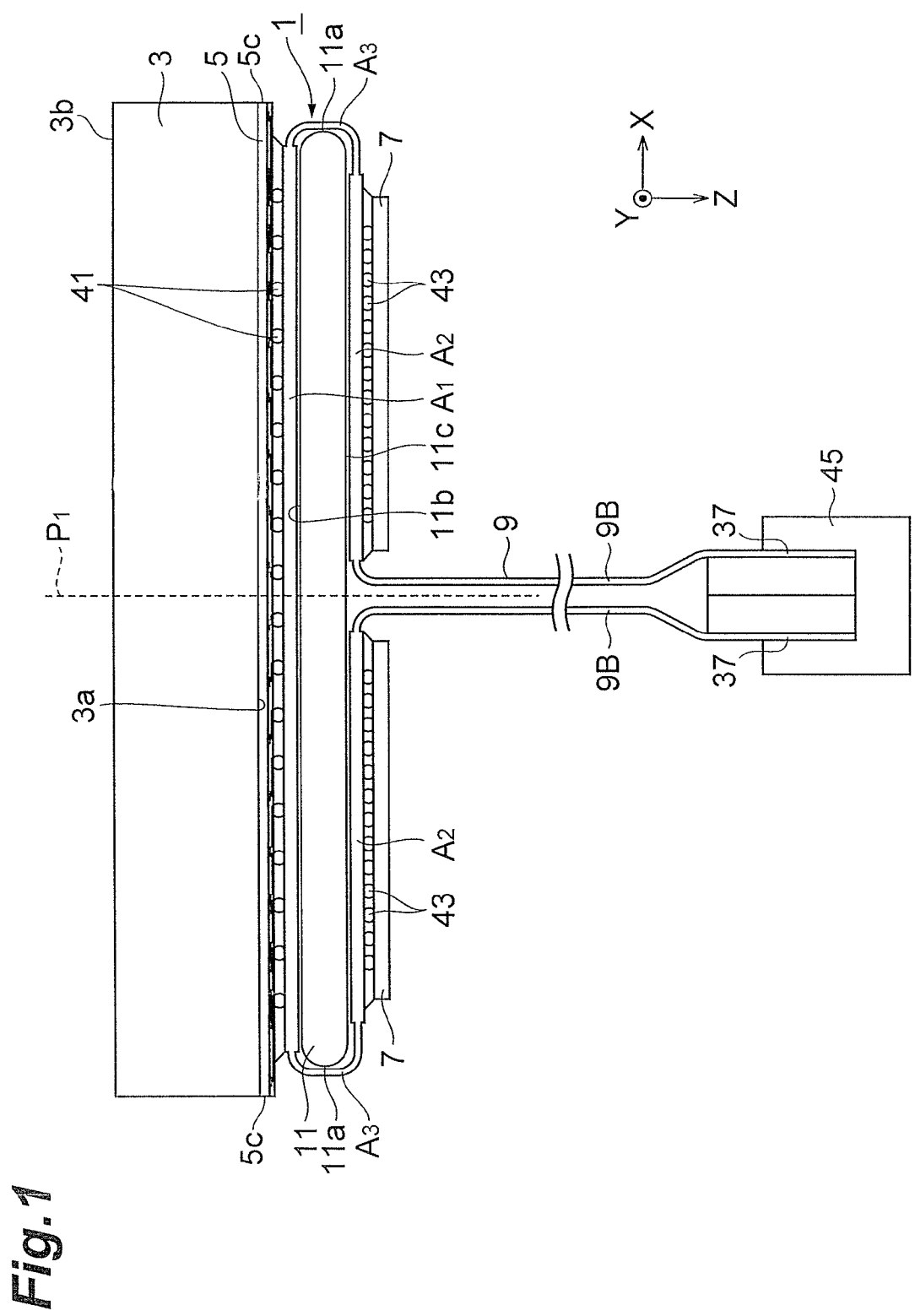
FIG. 1 is a front view of a radiation detecting unit according to a preferred embodiment of the present invention.

The preferred embodiments of the radiation detecting unit according to the present invention will be described below in detail with reference to the drawings. In the description of the drawings identical or equivalent portions will be denoted by the same reference signs, without redundant description. Each drawing was prepared by way of illustration and drawn particularly to emphasize objective portions for explanation. For this reason, dimensional ratios of each member in the drawings do not always coincide with those in practice.

FIG. 1 is a front view of radiation detecting unit 1 according to a preferred embodiment of the present invention. This radiation detecting unit constitutes a part of a radiation detecting apparatus while being attached to the interior of a CT device using radiation such as X-rays.

As shown in the same drawing, the radiation detecting unit 1 is used in optical connection and proximate arrangement to scintillator 3 through an optical coupling agent which is optically transparent to fluorescence from the scintillator 3, and is provided with a photodiode array (hereinafter referred to as PD array) 5 as a photoelectric conversion section, integrated circuits 7 as signal processing circuits to process signals from the PD array 5, a flexible substrate (FPC: Flexible Print Circuit Board) 9 as a flexible circuit board on which the PD array 5 and integrated circuits 7 are mounted, and a radiation shield plate 11. The scintillator 3 in proximate arrangement through the optical coupling agent to the radiation detecting unit 1 is a platelike member that converts radiation such as X-rays incident from a radiation entrance surface 3b opposite to an opposed surface 3a thereof, into light of predetermined wavelength and emits the light from the opposed surface 3a. The scintillator 3 is made, for example, using CsI doped with T1, and CsI has a structure consisting of a forest of many needle crystals (column crystals). In the description below, a direction perpendicular to the radiation entrance surface 3b is defined as Z-axis direction, and directions parallel to the radiation entrance surface 3b as X-axis direction and Y-axis direction.

The PD array 5 is arranged in proximity to the scintillator 3 through the optical coupling agent and is configured to convert rays emitted from the scintillator 3, into electric signals by photoelectric conversion and output the electric signals. This PD array 5 is electrically connected to the integrated circuits 7 through the flexible substrate 9, and the integrated circuits 7 receive the electric signals from the PD array 5 and subject the electric signals to an AD conversion process, an amplification process, a multiplexing process, and so on. The radiation shield plate 11 is a platelike member made of lead, tungsten, or the like and is disposed with the flexible substrate 9 in between the PD array 5 and the integrated circuits 7, in order to block leakage X-rays passing through the scintillator 3 and PD array 5 in the Z-axis direction, so as to prevent them from entering the integrated circuits 7.

Figure 2:
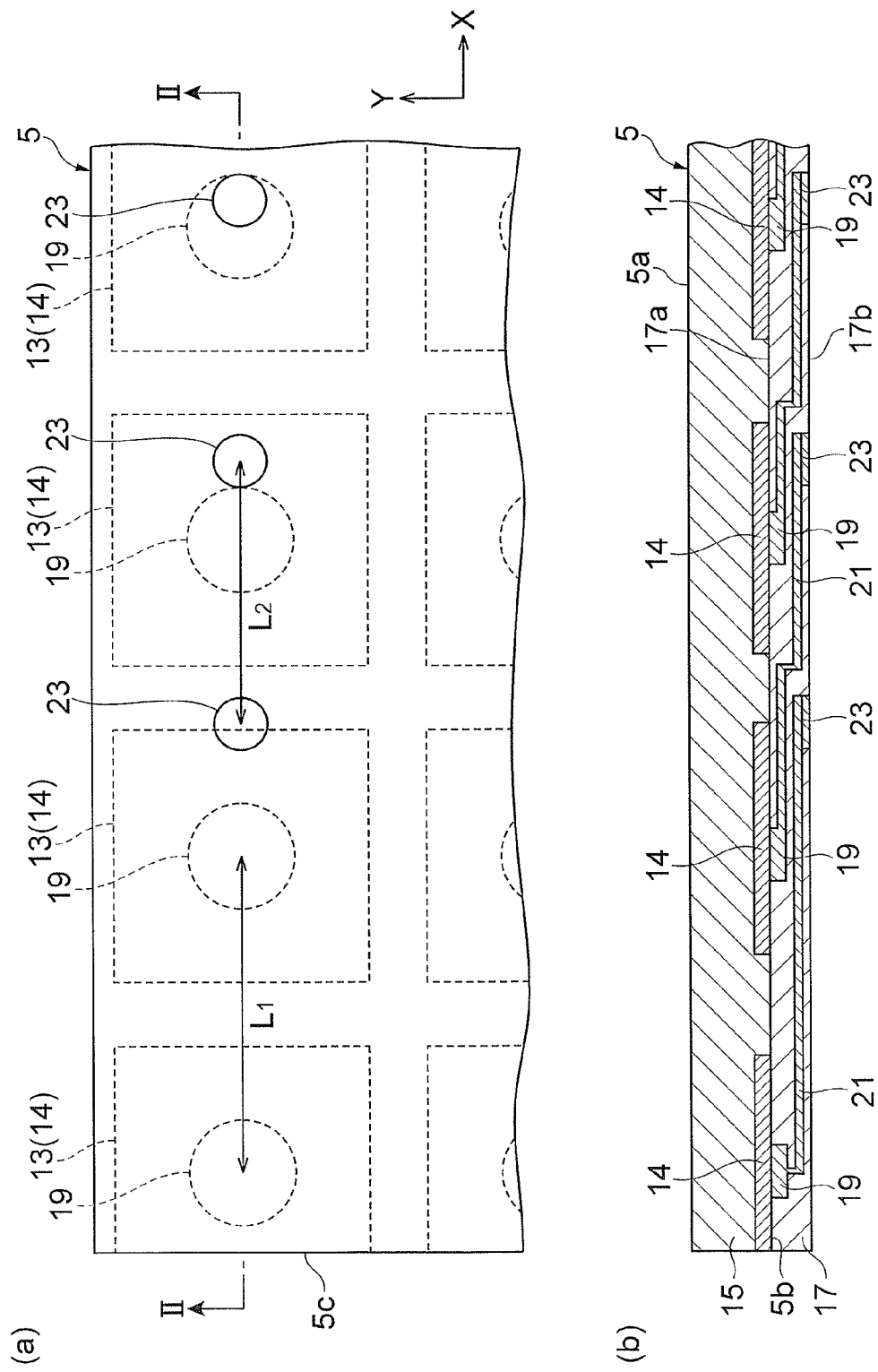
FIG. 2 (a) is a back view of a PD array shown in FIG. 1, when viewed from the opposite side to a light incidence direction and FIG. 2 (b) a cross-sectional view of the PD array of (a) along the line II-II.

Next, a configuration of the PD array 5 will be described in detail. In FIG. 2, (a) is a back view of the PD array 5 shown in FIG. 1, from the side opposite to the light entrance direction, and (b) a cross-sectional view of the PD array 5 of (a) along the line II-II.

A PD array chip 15 is a chip in which a plurality of second conductivity type impurity layers arrayed two-dimensionally in the X-axis and Y-axis directions are formed on one surface 5b of a first conductivity type semiconductor substrate and in which the first conductivity type semiconductor substrate and the second conductivity type impurity layers constitute photoelectric conversion elements. The PD array 5 including the photoelectric conversion elements as described above consists of the PD array chip 15 incorporating photodiode elements 13 as photoelectric conversion elements arrayed two-dimensionally in the X-axis and Y-axis directions, along a surface 5a opposed to the scintillator 3, and a wiring layer (multilayer wiring section) 17 laid on the surface 5b opposite to the surface 5a of the PD array chip 15.

In the PD array chip 15, the photodiode elements 13 of a back-illuminated type are arranged at an array pitch of a predetermined length $L_1$ along the X-axis direction, and on the surface 5b there are provided second conductivity type impurity layers 14 serving as anodes of the photodiode elements 13 and output electrodes 19 connected to the anodes of the photodiode elements 13, corresponding to positions of the respective photodiode elements 13. These output electrodes 19 are arranged at intervals of the array pitch $L_1$ along the X-axis direction, for output of electric signals generated by the respective photodiode elements 13.

The wiring layer 17 is a multilayer insulating film comprised of silicon dioxide ($SiO_2$) or the like and formed on the surface 5b of the PD array chip 15, and inside thereof there are wiring sections 21 electrically connected to the plurality of output electrodes 19 of the PD array chip 15. Specifically, the wiring sections 21 are formed in a connected state by laminate structure from junction portions to the output electrodes 19 on a surface 17a on the PD array chip 15 side of the wiring layer 17, to areas on a surface 17b opposite to the surface 17a of the wiring layer 17, and are electrically connected to output electrode pads 23 on the surface 17b. The wiring sections 21 are formed with gradual shift in a direction (+X-direction) from an end 5c along the array direction (X-axis direction) of the output electrodes 19 on the surface 5b toward the central part of the surface 5b, while extending from the surface 17a to the surface 17b. By this configuration, the array pitch in the X-axis direction of the output electrode pads 23 on the surface 17b is set to a length $L_2$ smaller than the length $L_1$ and the position of the output electrode pad 23 nearest to the end 5c is set nearer to the central part on the surface 5b than the output electrode 19 on the surface 5b of the PD array chip 15. Namely, this wiring layer 17 is a member for converting the array pitch of the output electrodes 19 of the PD array chip 15.

Figure 3:
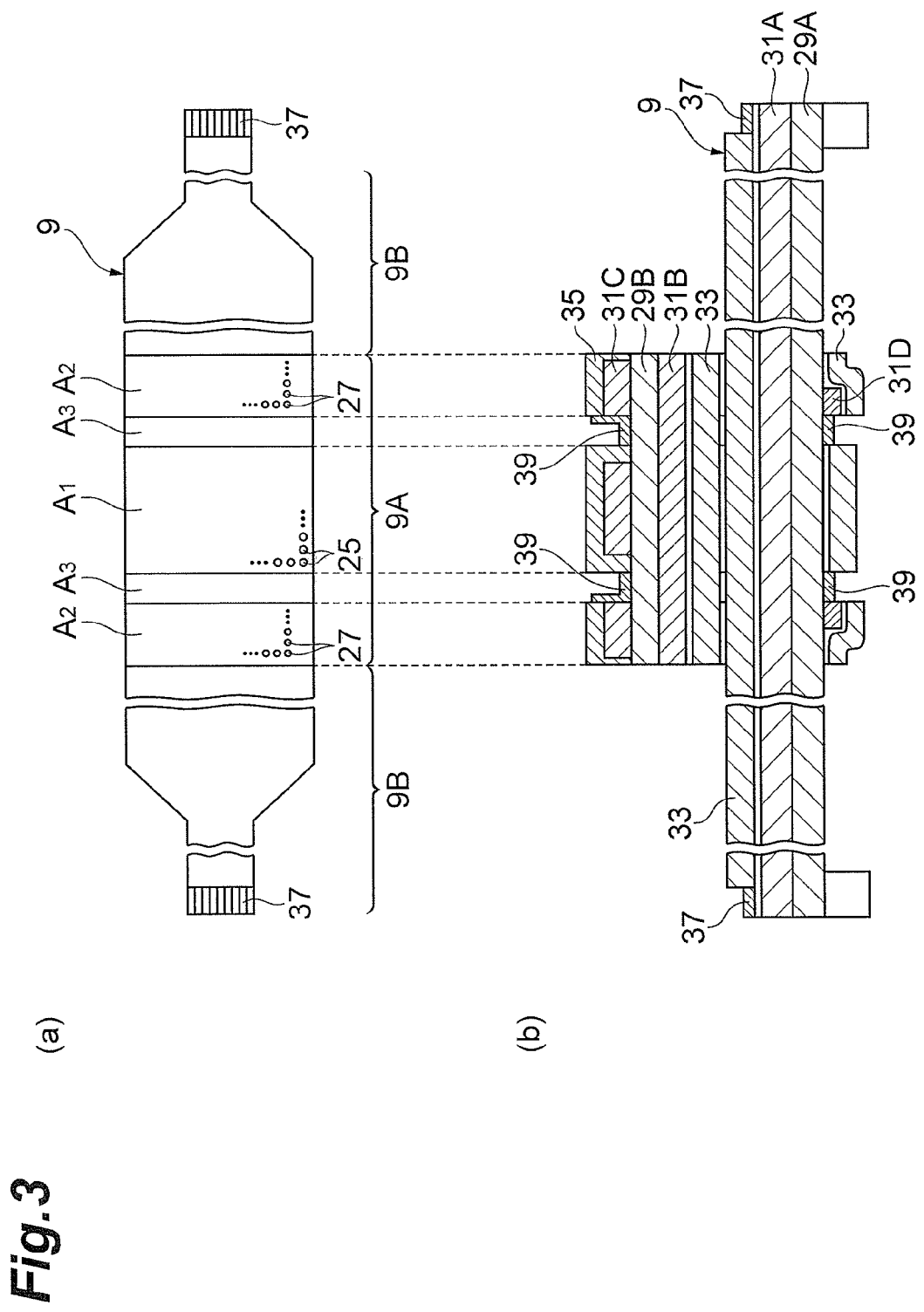
FIG. 3 (a) is a plan view of a flexible substrate of FIG. 1 when viewed from the circuit mounting surface side and FIG. 3 (b) a cross-sectional view along a longitudinal direction of the flexible substrate of (a).

In FIG. 3, (a) is a plan view of the flexible substrate 9 when viewed from the circuit mounting surface side and (b) a cross-sectional view along the longitudinal direction of the flexible substrate 9 of (a).

As shown in FIG. 3 (a), the flexible substrate 9 has a circuit mounting section 9A for mounting of the PD array 5 and integrated circuits 7, and two connector sections 9B formed integrally with the circuit mounting section 9A on both sides thereof. The circuit mounting section 9A has a rectangular region $A_1$ for mounting of the PD array 5 in a central part of a circuit mounting surface, and has two rectangular regions $A_2$ for mounting of the integrated circuits 7, on both sides of the region $A_1$ in the longitudinal direction of the flexible substrate 9. These regions $A_1$ and $A_2$ are provided with electrode pads 25 and electrode pads 27 for connection to the output electrode pads 23 of the PD array 5 and the integrated circuits 7, respectively. Furthermore, the circuit mounting section 9A has intermediate regions $A_3$ each between the region $A_1$ and either of the two regions $A_2$. The connector sections 9B are integrally formed outside the two regions $A_2$ of the circuit mounting section 9A and have a role for connection of the integrated circuits 7 to the outside.

With reference to FIG. 3 (b), the flexible substrate 9, as a whole, is composed of a stack of two layers made by forming metal layers 31A, 31B, 31C, and 31D of copper foil or the like on both surfaces of two base films 29A, 29B of insulating layers comprised of polyimide or the like, and further coating the metal layers with cover films 33, using an adhesive. Specifically, the base film 29B consisting of the stack of the metal layers 31B, 31C and the cover film 33 is bonded to a range corresponding to the circuit mounting section 9A on the base film 29A consisting of the stack of metal layers 31A, 31D and the cover films 33. Furthermore, a solder resist 35 of an insulating film is laid as a coating to cover the metal layers 31C on the circuit mounting surface side of the base film 29B.

The metal layers 31C on the base film 29B are generally composed of three separate portions as portions corresponding to the region $A_1$ and the regions $A_2$. The metal layers 31C each are independently connected so as to also serve as wiring patterns of the electrode pads 25 or the electrode pads 27 in the corresponding regions $A_1$ and $A_2$. Furthermore, the metal layers 31C are connected through unshown short via holes to the metal layer 31B also serving as a wiring pattern similarly, thereby functioning as wiring patterns for connection between the electrode pads 25 and the electrode pads 27 or, in other words, between the output electrode pads 23 of the PD array 5 and the integrated circuits 7. The metal layer 31A on the base film 29A is connected through short via holes to the metal layer 31B, thereby forming wiring patterns for connection between the electrode pads 27 and connector terminals 37 provided at respective tips of the connector sections 9B.

The metal layers 31C and the cover film 33 are not laid in part at portions corresponding to the intermediate regions $A_3$ of the flexible substrate 9 and the adhesive between the two layers of cover films 33 is also excluded there. Owing to this, the thickness of the intermediate regions $A_3$ of the flexible substrate 9 is set to be smaller than the thickness of the region $A_1$ and regions $A_2$. On the other hand, electromagnetic shield films 39 comprised of silver (Ag) or the like are formed at the portions corresponding to the intermediate regions $A_3$ on both surfaces of the flexible substrate 9. The electromagnetic shield films 39 may be formed by evaporation of metal or by application of a metal paste. The electromagnetic shield films 39 may be connected to a certain reference potential by the metal layers 31C of a corresponding pattern, to function as electromagnetic shield.

Referring back to FIG. 1, the PD array 5 is mounted on the region $A_1$ of the flexible substrate 9 of the above-described configuration in a state in which the output electrode pads 23 and the electrode pads 25 are connected through bump materials 41 of a solder, gold (Au), or the like. Furthermore, the integrated circuits 7 are mounted on the two regions $A_2$ of the flexible substrate 9 in a state in which the integrated circuits 7 and the electrode pads 27 are connected through bump materials 43. Furthermore, the radiation shield plate 11 is provided in proximity to the flexible substrate 9 so as to be opposed to the surface 5b of the PD array 5 (FIG. 2 (b)) with the flexible substrate 9 in between. The flexible substrate 9 with the PD array 5 and integrated circuits 7 thereon is folded at the portions corresponding to the intermediate regions $A_3$ thereof along the two ends 11a in the X-axis direction of the radiation shield plate 11, thereby covering the radiation shield plate 11 from the surface 11b thereof on the PD array 5 side to the surface 11c thereof opposite thereto. For this reason, the integrated circuits 7 are arranged on the opposite side to the PD array 5 with the radiation shield plate 11 in between when viewed from the direction along the Z-axis direction.

Figure 4:
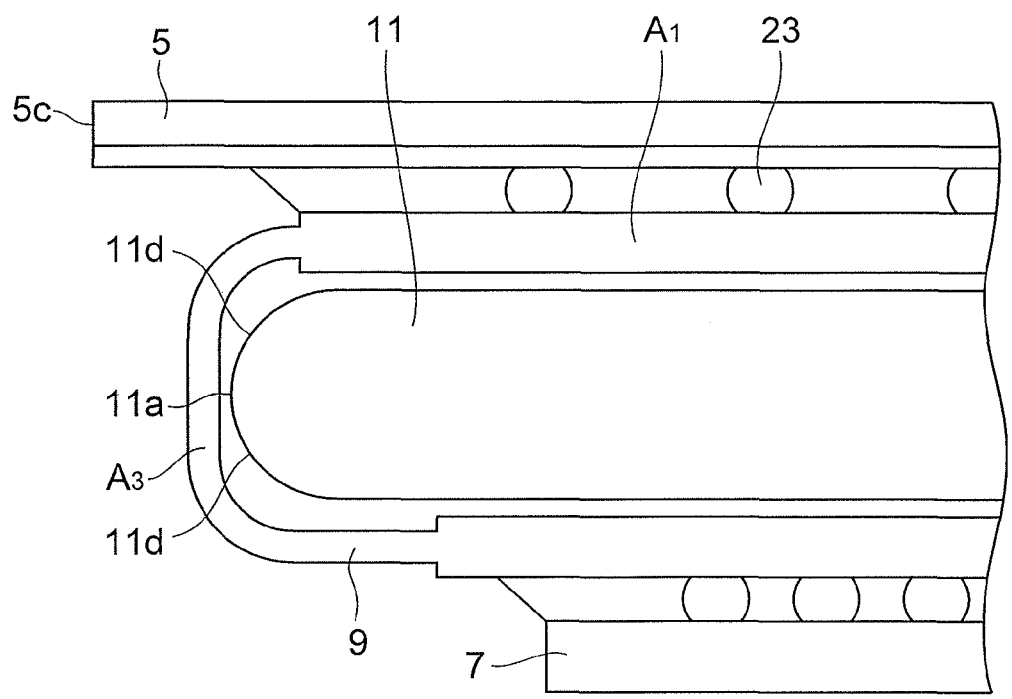
FIG. 4 is a front view showing an enlarged state of a part of the radiation detecting unit shown in FIG. 1.
Figure 4:
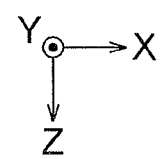

The width along the X-axis direction of the region $A_1$ of the flexible substrate 9 is set so as to be smaller than the width of the PD array 5. In conjunction therewith, the width along the X-axis direction of the radiation shield plate 11 is also set to be smaller than the width of the PD array 5 and the two ends 11a of the radiation shield plate 11 are located inside the two ends 5c of the PD array 5 within the surface 5b of the PD array 5. As a result, as shown in FIG. 4, when the flexible substrate 9 is folded along the ends 11a of the radiation shield plate 11, the flexible substrate 9 is kept from protruding to the outside from the ends 5c of the PD array 5. This reduction of the region $A_1$ is realized by the conversion function of the array pitch of the output electrode pads 23 by the wiring layer 17 formed in the PD array 5. The ends 11a of the radiation shield plate 11 are chamfered along the intermediate regions A3 of the flexible substrate 9, at corners 11d along the Y-axis direction. Such chamfering process may be C-shaped chamfering to linearly cut the corners 11d, or round chamfering to cut the corners into round surfaces.

Referring back to FIG. 1, the flexible substrate 9 has a virtually plane-symmetrical shape with respect to a plane $P_1$ parallel to the YZ plane, including a perpendicular passing the center of the surface 5b of the PD array 5. As a consequence, the two integrated circuits 7 are arranged at positions virtually symmetric with respect to the plane $P_1$, and the connector terminals 37 of the two connector sections 9B are located at nearly equal distances as distances along the flexible substrate 9 from the regions $A_2$ of the respective corresponding integrated circuits 7.

The below will describe a procedure of assembling the radiation detecting unit 1 as described above.

First, the radiation shield plate 11 is bonded to the surface opposite to the circuit mounting surface of the flexible substrate 9, with an adhesive such as resin, and then the adhesive is cured. Thereafter, the PD array 5 is mounted on the region $A_1$ of the flexible substrate 9 by bump connection. Then the two integrated circuits 7 are mounted on the two regions $A_2$ of the flexible substrate 9 by bump connection. Then an adhesive such as resin is applied onto the surface 11c of the radiation shield plate 11 opposite to the PD array 5. Furthermore, the flexible substrate 9 is folded toward the surface 11c of the radiation shield plate 11 at the intermediate regions $A_3$ to be joined to the surface 11c, and then the adhesive is cured. Thereafter, an underfill material is poured into the bump connection portions between the flexible substrate 9 and the PD array 5/the integrated circuits 7 and is then cured. Next, the tips of the connector sections 9B of the flexible substrate 9 are inserted into FPC connector 45 and then the scintillator 3 is secured on the light entrance surface 5a side of the PD array 5. Finally, characteristic and appearance inspections are carried out to complete the assembly of the radiation detecting unit 1.

Figure 5:
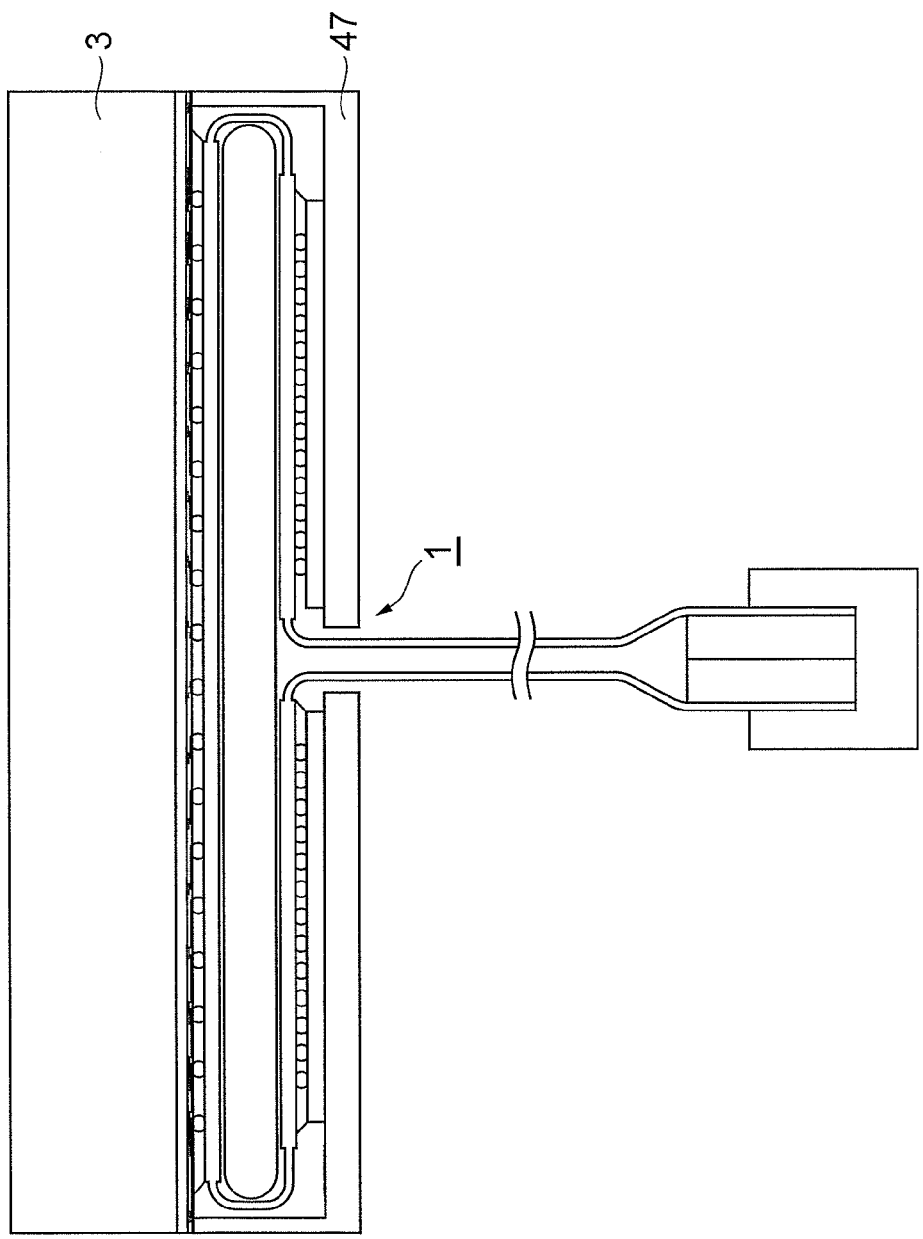
FIG. 5 is a front view showing a state in which a heat radiation lid is attached to the radiation detecting unit shown in FIG. 1.

On the occasion of arranging the radiation detecting unit 1 assembled as described above, into a CT device, as shown in FIG. 5, a heat radiation lid 47 of metal may be provided in a state in which it is bonded through a heat radiation grease to the edge of the PD array 5 and the surfaces of the integrated circuits 7 to be fixed so as to cover the radiation detecting unit 1. This heat radiation lid 47 is provided for heat radiation from the integrated circuits 7 and for positioning of the radiation detecting unit 1 in the CT device.

In the radiation detecting unit 1 described above, light of predetermined wavelength emitted from the scintillator 3 according to incidence of radiation such as X-rays is incident into the surface 5a of the PD array 5, the light is converted into electric signals by the plurality of photodiode elements 13 on the surface 5a, and the electric signals are sent from the output electrode pads 23 provided on the surface 17b corresponding to the photodiode elements 13, via the flexible substrate 9 to the integrated circuits 7. On that occasion, radiation passing through the photodiode elements 13 is blocked by the radiation shield plate 11 provided opposite to the PD array 5 with the flexible substrate 9 in between, thereby preventing adverse effects such as malfunction and failure on the integrated circuits 7. Furthermore, since the ends 11a of the radiation shield plate 11 are located inside the surface 17b of the PD array 5 and the array pitch of the output electrode pads 23 on the surface 17b of the PD array 5 is smaller than the array pitch of the photodiode elements 13 on the surface 5a, the connection range (mounting region) to the PD array 5 on the flexible substrate 9 is made narrower than the surface 17b and the flexible substrate 9 is folded along the ends 11a of the radiation shield plate 11, which eliminates the need for a space for routing of connection between the PD array 5 and the integrated circuits 7 outside the surface 17b of the PD array 5. This can prevent an insensitive zone from being produced between photoelectric conversion elements of adjacent units even in the case of tiling of radiation detecting units 1.

Figure 6:
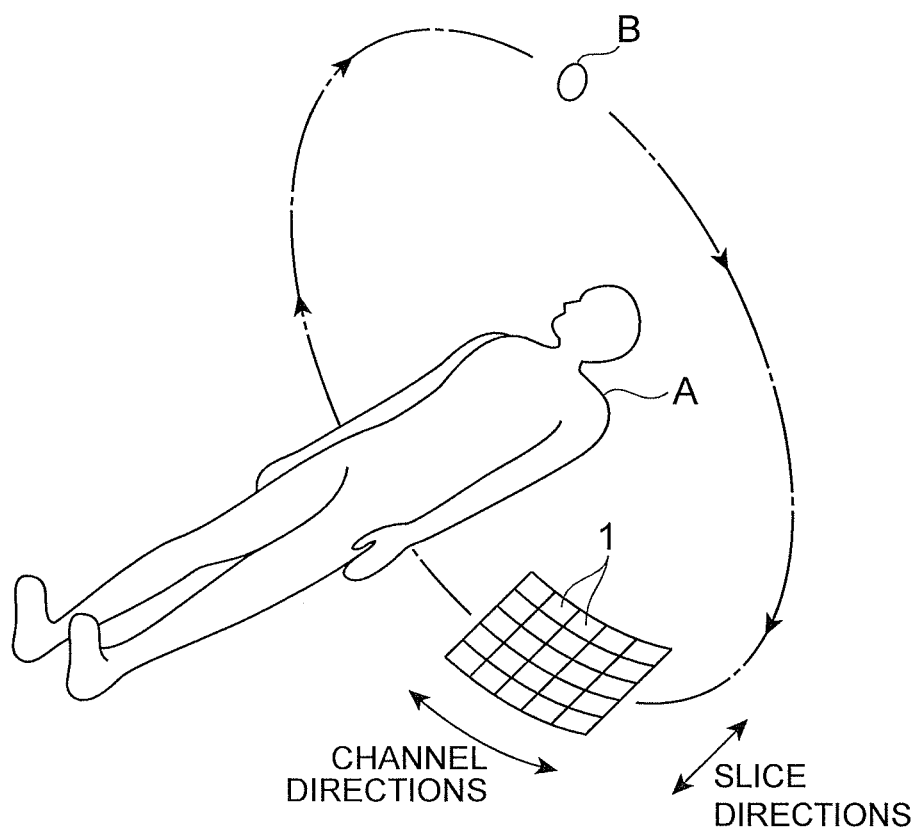
FIG. 6 is a conceptual diagram in a case where a plurality of radiation detecting units are arranged inside an X-ray CT device.

For example, FIG. 6 shows a conceptual diagram in a situation in which a plurality of radiation detecting units 1 are arranged inside an X-ray CT device. A gantry arranged inside the X-ray CT device is configured to rotate in an arrowed direction around a subject A. An X-ray generator B to generate X-rays toward the subject A is fixed to a part of the gantry. The plurality of radiation detecting units 1 are fixed on the opposite side of the gantry to the X-ray generator B, using an unshown attachment base. In this case, the plurality of radiation detecting units 1 are tiled in a two-dimensional array in channel and slice directions, and the dead area is minimized because there is no clearance between light receiving areas of adjacent units.

Since the electromagnetic shield films 39 are formed in the intermediate regions $A_3$ of the flexible substrate 9, when the plurality of radiation detecting units 1 are tiled, influence of electromagnetic noise from adjacent units is reduced on the integrated circuits 7, so as to prevent operation errors of the integrated circuits 7.

Furthermore, since the ends 11a of the radiation shield plate 11 are chamfered at the corners 11d along the intermediate regions $A_3$ of the flexible substrate 9, structural deterioration or the like is prevented in the intermediate regions $A_3$ of the flexible substrate 9 so as to improve durability.

Moreover, since the two integrated circuits 7 are mounted at the virtually symmetric positions with respect to the plane $P_1$ passing the center of the surface 5b of the PD array 5, on the flexible substrate 9 and the connector terminals 37 of the connector sections 9B are located at virtually equal distances from the mounted regions of the two integrated circuits 7, it is feasible to uniformize lengths of wiring paths from the photodiode elements 13 via the integrated circuits 7 to the connector terminals 37 and also uniformize wire capacitances, and it is thus feasible to stabilize output signals.

Yet furthermore, since the flexible substrate 9 is formed so that the thickness of the intermediate regions $A_3$ is smaller than the thickness of the mounting region $A_1$ of the PD array 5 and the mounting regions $A_2$ of the integrated circuits 7, the flexible substrate 9 can be readily folded at the intermediate regions $A_3$, while the strength of the mounting regions $A_1$, $A_2$ can be maintained.

Figure 7:
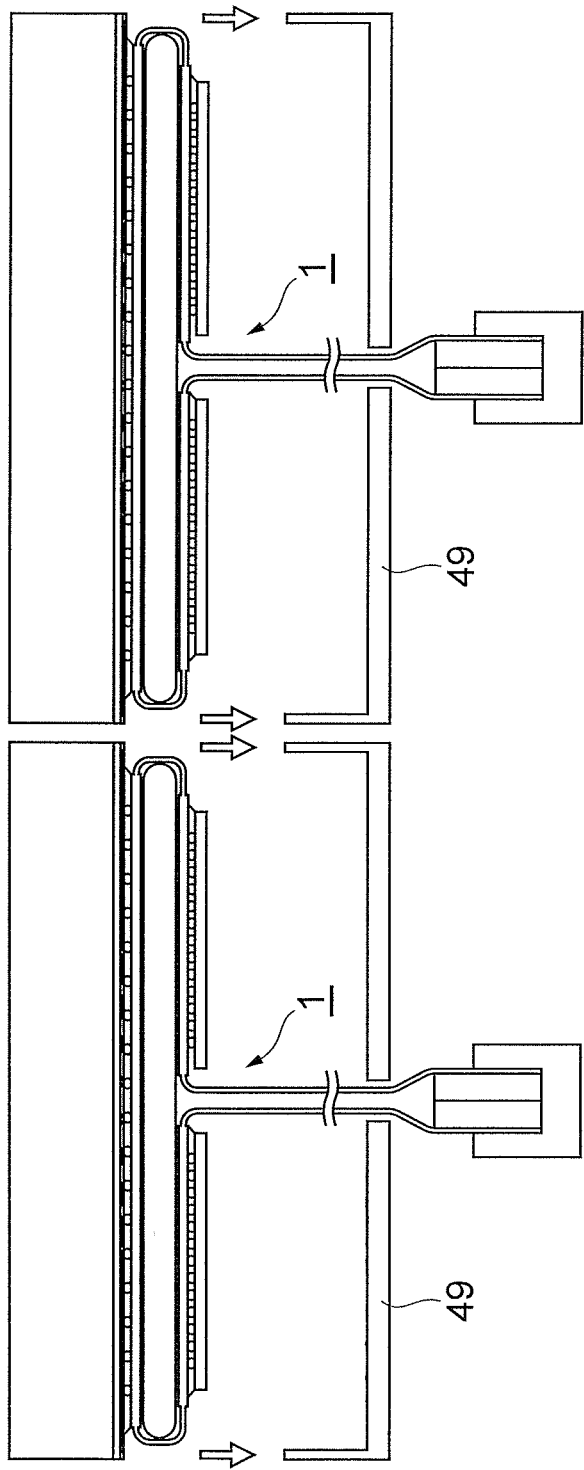
FIG. 7 is a front view showing another arrangement example of the radiation detecting units shown in FIG. 1, in a CT device.

The present invention is by no means limited to the above-described embodiment. The heat radiation lid was fixed to the radiation detecting unit 1, but a positioning member to the CT device may be provided with the function of the heat radiation lid. For example, as shown in FIG. 7, the radiation detecting units 1 may be positioned by attaching the plurality of radiation detecting units 1 to heat radiation lids 49 preliminarily fixed to the CT device. Instead of the electromagnetic shield films provided in the flexible substrate 9, the heat radiation lids 49 may be provided with the electromagnetic shield films.

Figure 8:
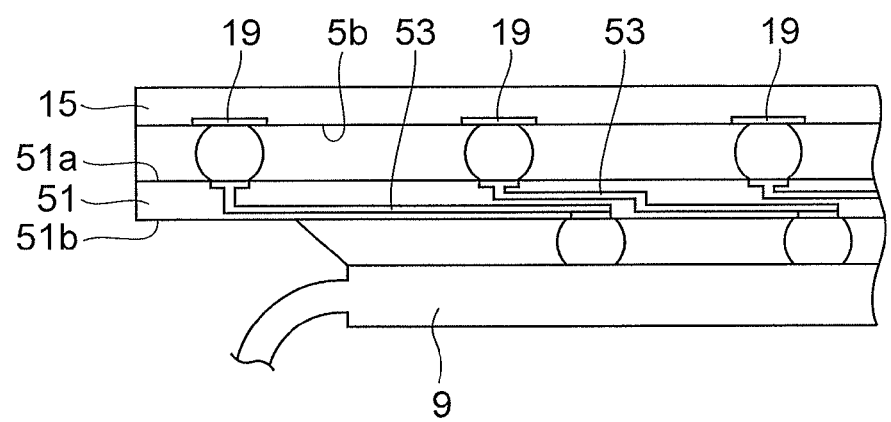
FIG. 8 is a front view showing a major part of a radiation detecting unit as a modification example of the present invention.

The wiring layer 17 was preliminarily formed in the PD array 5, but it is also possible to adopt a configuration wherein a separate member for conversion of electrode pitch is prepared and connected to the PD array 5. For example, as shown in FIG. 8, it can be contemplated that the output electrodes 19 on the surface 5b of the PD array chip 15 are connected through bump connection to one surface 51a of multilayer wiring substrate 51 as a separate member from the PD array chip 15 and the other surface 51b of the multilayer wiring substrate 51 is connected through bump connection to the flexible substrate 9. Wiring sections 53 for conversion of electrode pitch are formed between the surface 51a and the surface 51b in this multilayer wiring substrate 51.

It is preferable herein to provide the photoelectric conversion section with the multilayer wiring section for conversion of array pitch of electrodes on the second surface, as a wiring member. In this case, connection between the photoelectric conversion section and the flexible substrate can be readily realized.

It is also preferable to form the electromagnetic shield films in the intermediate regions of the flexible substrate. When this configuration is adopted, when a plurality of radiation detecting units are tiled, influence of electromagnetic noise from adjacent units can be reduced on the signal processing circuits.

Furthermore, it is also preferable to chamfer the ends of the radiation shield plate, at the corners along the intermediate regions of the flexible substrate. This configuration prevents deterioration or the like in the intermediate regions of the flexible substrate so as to improve durability.

Yet furthermore, preferably, the two signal processing circuits are mounted at virtually symmetric positions with respect to the center line of the second surface on the flexible substrate and the connector sections at virtually equal distances from the mounting regions of the two signal processing circuits are connected thereto. In this case, it is feasible to uniformize lengths of wiring paths from the photoelectric conversion elements via the signal processing circuits to the connector sections and also uniformize wire capacitances.

Moreover, it is also preferable to form the flexible substrate so that the thickness of the intermediate regions is smaller than the thickness of the mounting region of the photoelectric conversion section and the mounting regions of the signal processing circuits. By using such a flexible substrate, the flexible substrate can be readily folded at the intermediate regions, while the strength of the mounting regions can be maintained.

INDUSTRIAL APPLICABILITY

The present invention is applicable to usage as radiation detecting units and enables prevention of occurrence of an insensitive zone to radiation in parallel arrangement of multiple units.

LIST OF REFERENCE SIGNS

1 radiation detecting unit; 3 scintillator; 5 PD array (photoelectric conversion section); 5a light entrance surface (first surface); 5c ends; 7 integrated circuits (signal processing circuits); 9 flexible substrate; 9B connector sections; 11 radiation shield plate; 11a ends; 11d corners; 13 photodiode elements (photoelectric conversion elements); 17 wiring layer (multilayer wiring section); 17b surface (second surface); 23 output electrode pads; 51 multilayer wiring substrate (multilayer wiring section); $A_1$, $A_2$ mounting regions; $A_3$ intermediate regions.

The invention claimed is:

1. A radiation detecting unit comprising:

a photoelectric conversion section arranged in proximity to a scintillator and including a plurality of photoelectric conversion elements arrayed along a first surface opposed to the scintillator, and a plurality of electrodes for output of signals arrayed on a second surface opposite to the first surface corresponding to the plurality of photoelectric conversion elements;

a signal processing circuit for processing signals from the plurality of photoelectric conversion elements;

a flexible substrate on which the photoelectric conversion section and the signal processing circuit are mounted and which electrically connects the plurality of electrodes of the photoelectric conversion section to the signal processing circuit; and a radiation shield plate provided opposite to the second surface of the photoelectric conversion section with the flexible substrate in between and formed so that an end in a direction along the second surface is located inside the photoelectric conversion section, wherein the plurality of electrodes have an array pitch on the second surface made shorter than an array pitch of the photoelectric conversion elements by a wiring member, and wherein the flexible substrate is folded along the end of the radiation shield plate, at an intermediate region between a mounting region of the photoelectric conversion section and a mounting region of the signal processing circuit, whereby the signal processing circuit is arranged on the opposite side to the photoelectric conversion elements with the radiation shield plate in between.

2. The radiation detecting unit according to claim 1, wherein the photoelectric conversion section is provided with a multilayer wiring section for conversion of the array pitch of the plurality of electrodes on the second surface, as the wiring member.

3. The radiation detecting unit according to claim 1, wherein an electromagnetic shield film is formed in the intermediate region of the flexible substrate.

4. The radiation detecting unit according to claim 1, wherein the end of the radiation shield plate is chamfered at corners along the intermediate region of the flexible substrate.

5. The radiation detecting unit according to claim 1, wherein two said signal processing circuits are mounted at virtually symmetric positions with respect to a center line of the second surface on the flexible substrate and connector sections located at virtually equal distances from mounting regions of the two signal processing circuits are connected thereto.

6. The radiation detecting unit according to claim 1, wherein the flexible substrate is formed so that a thickness of the intermediate region is smaller than a thickness of the mounting region of the photoelectric conversion section and the mounting region of the signal processing circuit.

\* \* \* \* \*